United States Patent [19]

Hall et al.

[11] 4,202,666
[45] May 13, 1980

[54] METHOD AND APPARATUS FOR PREVENTING THE DESTRUCTION OF AN ALKALI SOURCE OF A NITROGEN-PHOSPHOROUS DETECTOR

[75] Inventors: Randall C. Hall, Round Rock; Burney J. Ehrlich, Austin, both of Tex.

[73] Assignee: Tracor, Inc., Austin, Tex.

[21] Appl. No.: 880,974

[22] Filed: Feb. 24, 1978

[51] Int. Cl.² ............... G01N 27/62; G01N 31/08
[52] U.S. Cl. ................ 23/232 E; 23/232 C; 422/54; 422/96
[58] Field of Search ............. 23/232 E, 232 C; 422/54, 95, 96, 98

[56] References Cited

U.S. PATENT DOCUMENTS

| 3,423,181 | 1/1969 | Dimick et al. | 422/54 |
|---|---|---|---|
| 3,425,806 | 2/1969 | Karmen | 422/54 X |
| 3,438,243 | 4/1969 | Parks, Jr. et al. | 73/231 |
| 3,535,088 | 10/1970 | Zimmermann | 422/54 |
| 3,547,588 | 12/1979 | Miyamoto et al. | 23/232 E |
| 3,589,869 | 6/1971 | Scolnick | 23/232 E |
| 3,607,096 | 9/1971 | Hartmann | 422/54 |
| 3,684,454 | 8/1972 | Martin et al. | 23/232 E X |
| 3,789,190 | 1/1974 | Orosy et al. | 219/497 |
| 3,850,579 | 11/1974 | Dubsky | 422/54 |
| 3,852,037 | 12/1974 | Kolb et al. | 422/54 |
| 3,866,587 | 2/1975 | Knapp | 219/499 X |
| 3,879,985 | 4/1975 | Maslen | 73/27 R |
| 3,911,386 | 10/1975 | Beaudoin et al. | 422/94 X |

FOREIGN PATENT DOCUMENTS 1274456  5/1972  United Kingdom .................. 422/54

Primary Examiner—Joseph Scovronek
Attorney, Agent, or Firm—Arnold, White & Durkee

[57] ABSTRACT

A method and apparatus for preventing the destruction of an alkali source in a nitrogen-phosphorus detector by certain reactive and derivatizing reagents encountered in gas chromatography is disclosed. Protection is afforded by lowering the temperature of an electrically heated alkali source during the period in which offensive substances in a gas under analysis are eluted, with the temperature of the source being restored after passage of the offensive substances. The temperature of the alkali source is changed by altering the current through an electrical resistance heater with a temperature control circuit that utilizes a wheatstone bridge.

9 Claims, 1 Drawing Figure

METHOD AND APPARATUS FOR PREVENTING THE DESTRUCTION OF AN ALKALI SOURCE OF A NITROGEN-PHOSPHOROUS DETECTOR

BACKGROUND OF THE INVENTION

This invention relates to alkali source ionization detectors used in gas chromatography. More specifically, this invention relates to the protection of an alkali source ionization detector from adverse effects resulting by reason of contact with contaminants or reactive agents passing through the detector.

In gas chromatography, a multicomponent sample is separated in the gas chromatographic column and eluted with a carrier gas in order to isolate the components of the original sample as mixture with the carrier gas. This eluate is conducted to any one of a number of detectors, such as flame ionization detectors and the like. One type of ionization detector utilizes an alkali source in the ionization chamber to contact the effluent of the column as it is eluted. Certain compounds, for example nitrogen and phosphorus compounds, produce ionic emissions when contacted with a heated alkali source. The collection of these ionic emissions and the measurement of the resulting ionic current can provide a quantitative indication of these specific compounds.

Recent advances have been made in alkali sensitized detectors for gas chromatography. One significant improvement has been the utilization of electrically heated alkali sources to stabilize the response characteristics of alkali sensitized detectors. Previously, alkali source detectors employed a small hydrogen/air flame for volatilization of an alkali salt and initiation of the reaction mechanism that produced the detector signal. However, since the sensitivity of such early detectors was dependent upon the temperature of the alkali material, these detectors exhibited instabilities due to fluctuating flame temperatures.

An electrically heated alkali source provides for more accurate control of the temperature of an alkali source, resulting in greater stability of the detector. In electrically heated alkali source detectors, a mixture of alkali salts in a silica gel matrix is fused to a heating element, the temperature of which is maintained by a regulated power supply.

At elevated temperatures of 700° C. or higher, alkali sources are easily damaged by certain solvents and derivatizing reagents that are commonly used in gas chromatography. Contact with such solvents can result in damage to the heating element and/or the alkali source. For example, the alkali of the source can be unduly depleted due to the formation of volatile alkali halides when a halogen containing solvent is passed through the cell. Alkali sources can also be destroyed by derivatizing reagents used to prepare the sample such as N,O-bis-(trimethylsilyl)-acetamid (known as "BSA") that are decomposed by the hot source and covered with decomposition products. See Gehrke, et al, U.S. Pat. No. 3,415,864. Therefore, it is desirable to protect the alkali source during the period of passage of such potentially damaging materials.

Typically, halogen solvent and derivatizing agents have a low retention time in a chromatograph column. Accordingly, these materials are among the first materials to exit the column following injection of the sample, and their passage period is predictable.

At present, if potentially damaging materials are to be used, a four-port valve is employed to divert the carrier gas stream away from the detector during the elution of the potentially offensive materials. However in many instances, utilization of a valve is not an ideal solution since it is expensive, introduces dead volume, introduces additionally reactive surfaces which must be protected, and increases the number of components that require attention. Jahnsen et al, U.S. Pat. No. 3,859,209 teaches the use of two multi-port valves to divert organic chemical compounds.

In Giuffrida, U.S. Pat. No. 3,372,994, the use of an alkali-metal salt fused to an electrode and heated by a hydrogen flame is disclosed. The alkali coating allows the detector to selectively emphasize phosphorus-containing organic compounds in mixtures.

Kolb et al, U.S. Pat. No. 3,852,037, addresses the deterioration problem attendant the use of an alkali glass bead which is maintained in a heated, softened state by a hydrogen flame during operation of the detector. Kolb teaches the use of a sensing electrode located above the alkali glass bead, with the electrical conductivity between the bead and the electrode being measured to indicate deterioration of the glass bead. A continuous supply of alkali is made available as the surface area of the glass bead gradually deteriorates.

SUMMARY OF THE INVENTION

In accordance with this invention, an electrically heated alkali source is reduced in temperature during the period of elution of potentially damaging materials. The temperature is reduced to a level below that which promotes destructive reactions on the source, but is maintained sufficiently high to preclude the condensation of non-volatile materials on the source. The reduction in temperature of the electrical heater is referred to as "desensitization" of the source.

In accordance with a more particular aspect of the present invention, the source temperature is varied by regulating the current through an electrical resistance heater on which an alkali source is mounted. One means for regulating current through the resistance heating element comprises a wheatstone bridge having the alkali source and electrical resistance heater arranged as one leg of the bridge. A fixed resistance value is connected in each of the remaining three legs of the bridge. Additional means is included to selectively change the voltage divider ratio of one side of the bridge to reduce the voltage drop across the resistance heater, reducing the current therethrough and lowering the source temperature from the first elevated temperature to the second lower temperature. The means for changing the voltage divider ratio of one side of the bridge can be an external resistance which is connectable in parallel with a leg of the bridge that does not include the source. When offensive substances are about to pass the alkali source, a control element coupled to the external resistance is actuated manually or by timed means to connect the external resistance and desensitize the alkali source.

A resistance heating element having a resistance proportional to its temperature is preferably utilized. Accordingly, the means for regulating the current through the electrical heater element may function in response to the resistance value of the heater element. To so operate, the means for regulating current flow through the heater element may further comprise a differential amplifier or comparator connected across the output terminals of the bridge. The differential amplifier or comparator detects and amplifies a potential appearing across the bridge output terminals due to an unbalanced condition. The output of the amplifier is applied to a series regulator supplying power to the bridge.

When the control element is actuated connecting the external resistance in parallel with a leg of the bridge, the bridge becomes unbalanced, and a voltage difference results across the output terminals. To balance the bridge, the resistance of the electrical heater must be varied. A variation in resistance of the electrical heater needed to balance the bridge is achieved by varying the voltage applied across the bridge by the series regulator. For example, a reduction in bridge voltage causes a corresponding reduction in the voltage across and the current through the source heater. As a result, the electrical heating effect is reduced and the temperature of the source decreases. As the source temperature decreases, so does its resistance, which continues until the bridge is once again in balance. The alkali source temperature is lowered and is, therefore, desensitized from the offensive substances that would otherwise damage it.

BRIEF DESCRIPTION OF THE DRAWINGS

The FIGURE illustrates an electrical schematic block diagram of circuitry including a wheatstone bridge and associated components for varying the temperature of an alkali source between upper and lower temperature limits.

DETAILED DESCRIPTION OF A PREFERRED EMBODIMENT

Figure 1:
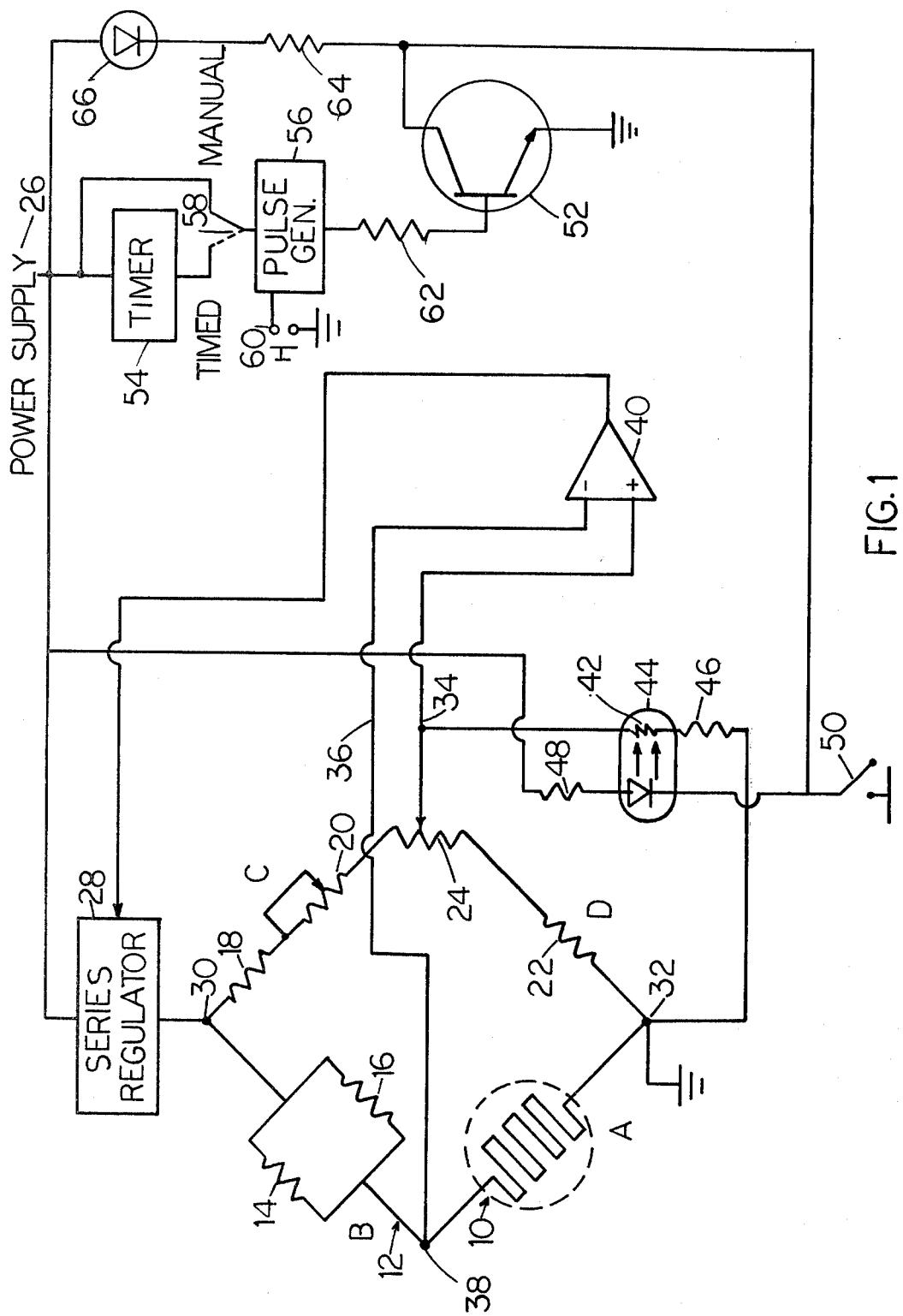

The FIGURE is a simplified schematic diagram of circuitry suitable for use in gas chromatograph detector apparatus that utilizes an electrically heated alkali source to implement the present invention.

The alkali source 10 is preferably a mixture of alkali salts in a silica gel matrix fused to an electrical resistance heater element. Alkali source 10 is heated by current flow through a resistance heating element.

In normal operation of an alkali sensitized gas chromatograph detector used for the determination of trace quantities of nitrogen and phosphorous containing compounds, the source temperature is maintained at approximately 700° C. To prevent damage to the source and-/or heater element by certain solvents and derivating agents used in gas chromatography, means is provided in accordance with the present invention for selectively varying the temperature between the normal operating temperature and a lower temperature that is below the temperature at which destructive reactions occur, but above the temperature at which non-volatile materials would condense on the source. For the more commonly encountered destructive reactants, a reduction of source temperature to about 400° C. has been found satisfactory.

Suitable means for achieving the desired result of source desensitization can take on many forms. However, since source temperature control is typically provided for accurately controlling the temperature of the source, means for varying the source temperature will be most conveniently incorporated therein. Further, inasmuch as source temperature is controlled by varying the current through the heater element, means for varying the source temperature between the aforementioned levels will be most conveniently achieved by regulating the voltage applied across the heater element.

To provide accurate monitoring of source temperature, the heater element desirably is one, such as platinum wire, having a resistance value that varies substantially in proportion to heater element temperature. With such characteristics, the heater element can effectively be used as a feedback device directly indicating source temperature. The circuitry shown in the FIGURE is for use in gas chromatograph detector apparatus having an alkali source that is heated by a heating element with such temperature-resistance characteristic.

The particular means shown in the FIGURE for varying the source 10 temperature between the prescribed levels establishes a prescribed flow of electrical current through the electrical resistance heater in response to its resistance value to effect temperature level control. The preferred embodiment shown utilizes a wheatstone bridge circuit 12 to detect variations in the resistance of heater/source 10 and provide an output signal indicative thereof.

As shown in the schematic diagram, the electrically heated source 10 is connected in leg A of wheatstone bridge 12. Leg B of bridge 12 is a resistance comprising resistors 14 and 16 arranged in parallel. Leg C comprises a resistance 18 and a trim pot 20. Leg D comprises a resistance 22. Legs C and D are interconnected by a variable voltage divider 24, the wiper contact of which serves as one output terminal of bridge 12.

Power to bridge 12 is applied from power supply 26 via a controlled series regulator 28, such as a darlington pair. Current through series regulator 28 is applied to bridge 12 at node 30, which is the interconnection of leg B to leg C. The voltage across bridge 12 established by regulator 28 is measurable between node 30 and node 32 at the interconnection of legs A and D.

The output voltage from bridge 12 is available via output terminals 34 and 36. Terminal 34 is the wiper contact of variable voltage divider 24, and terminal 36 is a connection to node 38 at the interconnection of legs A and B. Output terminals 34 and 36 are connected to differential amplifier or comparator 40, the output of which is applied as the controlling signal for series regulator 28.

Any imbalance of bridge 12 will produce a voltage differential between output terminals 34 and 36 that is detected by amplifier 40. During an unbalanced condition, amplifier 40 outputs a voltage level that causes regulator 28 to modify the voltage across the bridge between nodes 30 and 32 in an attempt to balance the bridge.

An unbalanced condition will occur when the resistance in any leg of the bridge is changed. With the exception of heater/source 10 resistance all resistances in the bridge, once trim pot 20 and variable voltage divider 24 are set, are fixed in value. Preferably, the resistances in legs B, C and D have a low coefficient of thermal resistance and, therefore, vary negligibly with temperature.

The mathematical relationship of a wheatstone bridge at balance is defined by the following expression with respect to the FIGURE:

$$R(\text{leg B}) \times R(\text{leg D}) = R(\text{leg A}) \times R(\text{leg C})$$

The effective resistance of parallel resistors 14 and 16 in leg B is equated to the appropriate resistance of electrical heater and source 10 in leg A, when the temperature of the source is at the normal operating temperature. Accordingly, to balance bridge 12 the resistance of leg C must equal the resistance of leg D, thereby providing the same voltage divider ratio as that established by legs A and B.

Since the resistance in each of the legs of the bridge, except the electrical heater/source 10 in leg A, is a fixed resistance value following an initial calibration of trim pot 20 and variable voltage divider 24, an imbalance of bridge 12 can result only from a variation in the resistance value of the heater/source 10. Since the resistance value of the heater/source 10 is proportional to the temperature of the source, a change in resistance from the desired value, which would balance the bridge and establish the source at the proper operating temperature, will cause a voltage to appear across the output terminals of bridge 12. Accordingly, if the temperature of source 10 increases above the desired operating temperature, causing the resistance in leg A of the bridge to increase, the bridge will become unbalanced and a voltage differential will be detected by comparator 40.

The output voltage of comparator 40 will, in response to a bridge output voltage indicative of an increase in source temperature, change in a manner so as to drive series regulator 28 to reduce the voltage applied across the bridge between nodes 30 and 32. A reduction in voltage across the bridge lowers the current through each side of the bridge. A reduction in the current flowing through leg A reduces the temperature of the heater element and source 10, which correspondingly causes a reduction in resistance value. And as the resistance value in leg A of the bridge decreases, so does the differential voltage appearing across the bridge output terminals. The reduction in bridge output voltage is detected by comparator 40 and the output control signal to the series regulator is accordingly adjusted until the bridge is again balanced and a stabilized source temperature condition is established at the desired operating point.

In order to accomplish the desired desensitization of source 10 while reactive substances are passing through the detector apparatus, and to subsequently restore the source to the elevated temperature, the particular means shown in the FIGURE for varying the temperature of source 10 further comprises means to selectively unbalance the bridge. Such means in the preferred embodiment is one that changes the voltage divider ratio of the side of the bridge not containing the heater element and source.

Since it is desired to reduce the temperature of the source, rather than further increase the temperature, the voltage divider ratio established by the resistance values in legs C and D of the bridge must be changed to reduce the effective resistance value of leg D. Accordingly, the means to unbalance the bridge by changing the bridge voltage divider ratio can suitably be an electrical resistance element 42 which is selectively connectable in parallel with the resistance already in leg D of the bridge. Further, the means preferably includes a control element for connecting and disconnecting the electrical resistance element.

In the particular embodiment illustrated in the FIGURE, the control element is an opto-electric coupler 44 comprising a light emitting diode and photosensitive resistor. The photosensitive resistor portion of coupler 44 is connected in series with an external resistor 46, with the series combination being connected between the wiper of variable voltage divider 24 and node 32 of the bridge. The light emitting diode portion of coupler 44 is connected in series with a current limiting resistor 48 that is further connected to the power supply for the circuitry. The cathode of the light emitting diode is connectable to ground through either a manually actuable switch 50, or by timer means comprising a transistor driver 52 to be discussed more completely herein.

Desensitization of source 10 is accomplished by the circuitry in the FIGURE when resistance 46 is connected in parallel with leg D of the bridge, which reduces the effective resistance thereof. The voltage divider ratio formed by legs C and D of the bridge is altered in a manner that produces a voltage differential across the bridge output terminals that simulate the condition of excess temperature of source 10. Accordingly, comparator 40 drives series regulator 28 to decrease the voltage applied across the bridge, causing a corresponding decrease in current through leg A. As outlined previously, a decrease in current in the electrical heat resistance heater in leg A of the bridge reduces the temperature of source 10 with a reduction in heater element resistance following it. When the source temperature falls to the desired level, as indicated by a resistance value for the heater element and source that corresponds to such temperature, the bridge will be balanced.

Upon disconnecting parallel resistance 46, the voltage across the resistance in leg D will immediately increase, causing an imbalance of the bridge. Comparator 40 and series regulator 28 react to the imbalance, which is an indication of low source temperature, to increase the voltage across the bridge and correspondingly increase current through leg A. The increase in current through leg A causes the source temperature to increase until the normal operating temperature is restored.

When the light emitting diode portion of coupler 44 is turned off, photosensitive resistor portion has a high resistance which keeps the parallel circuit comprising external resistor 46 open. When the light emitting diode is energized, the resistance of the photosensitive resistor falls to a low, negligible value such that external resistor 46 is connected in parallel with leg D of the bridge.

In addition to the means for selectively varying the alkali source temperature, means can also be provided for controlling the source temperature varying means to selectively reduce the temperature of the alkali source from the higher temperature to the lower temperature during the time that alkali reactive substances are passing through the detector and subsequently restore the source temperature to the higher level. Such control means can be timed means that causes the source temperature varying means to reduce the source temperature for a set period of time.

In the schematic diagram of the FIGURE, timer 54 provides a control voltage to pulse generator 56 via manual switch 58. A spring button switch 60 on pulse generator 56 initiates the operation thereof. The output of pulse generator 56 is applied to switching transistor 52 via base resistor 62. A resistor 64 and diode 66 are connected to the collector lead of transistor 52. Both timer 54 and pulse generator 56 may comprise a Signetics NE555 integrated circuit device.

Either a manual or timed mode is selectable by way of switch 58. In the manual mode, pulse generator 56 turns on transistor switch 52 upon being initiated by push-button 60. The anode of the light emitting diode in electro-optical coupler 44 is taken to ground potential, thereby forward biasing the light emitting diode and closing the parallel resistance circuit. In the timed mode, pulse generator 56 is controlled by timer 54 to turn on transistor 52 for the prescribed period of time. The timed period begins when push button 60 is depressed initiating preparation of pulse generator 56. When the timed period expires, timer 54 turns off pulse generator 56. Timed periods are typically from 5 to 120 seconds.

The foregoing description has been directed to a particular preferred embodiment of the present invention for purposes of explanation and illustration. It will be apparent, however, to those skilled in this art that the invention admits to embodiment in many forms. For example, the means for selectively varying the temperature of the alkali source may comprise other types of circuitry for regulating the flow of electrical current through an electrical resistance source heater other than the wheatstone bridge shown. Further, feedback sensing for establishing the elevated operating temperature and the reduced, non-reactive temperature of the source can be other than in response to a change in resistance of the electrical heater; for example, a thermocouple can be utilized to provide a feedback signal indicative of source temperature. These and other embodiments of the invention will be apparent to those skilled in this art. It is the intention that the following claims cover all such equivalent modifications and variations as fall within the scope of the invention.

What is claimed:

1. In a method of chromatographic analysis utilizing an alkali sensitized ionization detector, the steps of:

reducing the temperature of the alkali source from a first, elevated temperature at which active analysis is performed to a second, lower temperature that is below the temperature at which reactive substances would react with the source, but is above the temperature at which condensation of non-volatile materials on the source occurs, said reduction in temperature being made during the time that reactive substances are passing through the detector; and restoring the source temperature to the elevated temperature after the reactive substances have been eluted.

2. An ionization detector for chromatographic analysis, which comprises:

an electrically heated alkali source comprising an alkali source fused to an electrical resistance heater element having a resistance value that varies substantially in proportion to its temperature;

a bridge circuit having the electrical resistance heater element connected in one branch thereof, the bridge circuit being responsive to an application thereto of electrical power to produce a flow of electrical current through the heater element that effects heating of the alkali source and produces a signal indicative of the imbalance of the bridge;

means responsive to the signal for adjusting the electrical power applied to the bridge circuit to control the flow of electrical current through the heater element so as to set the temperature of the alkali source and establish a resistance value of the heater element that balances the bridge; and means for selectively unbalancing the bridge circuit to effect a change in the temperature of the alkali source from a first elevated temperature at which active analysis is performed to a second, lower temperature that is below the temperature at which reactive substances passing through the detector will react with the alkali source, but is above the temperature at which condensation of non-volatile materials on the source occurs, and to effect a change after passage of the reactive substance that restores the temperature of the alkali source to the elevated temperature.

3. The detector of claim 2 wherein:

the bridge circuit is a Wheatstone bridge having the electrical resistance heater element connected in one leg and a fixed resistance in each of the other legs of the bridge;

the bridge unbalancing means includes an electrical resistance element connectable in parallel with a leg of the Wheatstone bridge that does not include the electrical resistance heater element to change the voltage divider ratio of one side of the Wheatstone bridge and means for effecting selective connection and disconnection of the electrical resistance element.

4. The detector of claim 3 further comprising:

a timer for actuating the connection means to connect the electrical resistance element for a prescribed period of time.

5. The detector of claim 3 wherein:

the connection means is an opto-electric coupler comprising a light emitting diode and a photosensitive resistor, the photosensitive resistor being connected in series with the electrical resistance element.

6. An ionization detector for chromatographic analysis, which comprises:

an electrically heated alkali source comprising an alkali source fused to an electrical resistance heater;

a bridge circuit having the electrical resistance heater connected in one branch of the bridge circuit, the bridge circuit being adapted for connection to a source of electrical power to establish a flow of electrical current through the source heater and thereby produce heating of the alkali source;

an electrical resistance element connectable to the bridge circuit for altering the flow of electrical current through the source heater;

a control element coupled to the electrical resistance element for effecting connection and disconnection of the resistance element to the bridge circuit to effect a a change in the flow of electrical current through the source heater that reduces the temperature of the alkali source from a first elevated temperature at which active analysis is performed to a second, lower temperature that is below the temperature at which reactive substances passing through the detector will react with the alkali source, but is above the temperature at which condensation of non-volatile materials on the source occurs, and to effect a subsequent change in the flow of electrical current through the source heater after passage of the reactive substance that restores the temperature of the alkali source to the elevated temperature.

7. The detector of claim 6 further comprising:

means coupled to the control element for actuating the control element during passage of alkali reactive substances through the detector to connect the electrical resistance element.

8. The detector of claim 6 wherein:

the control element is an opto-electric coupler including a photosensitive resistor connected in series with the electrical resistance element.

9. An ionization detector for chromatographic analysis, which comprises:

an electrical resistance heater element, the heater element having a resistance value that varies substantially in proportion to its temperature;

an alkali source fused to the heater element;

a Wheatstone bridge circuit having the heater element connected in one leg of the bridge and a fixed resistance connected in each of the other legs of the bridge;

a controllable power supply connected to the bridge for producing a flow of electrical current through the legs of the bridge to effect heating of the alkali source and to produce a differential voltage across the bridge indicative of bridge balance;

means connected across the Wheatstone bridge and responsive to the differential voltage for detecting an imbalance of the bridge and producing an output signal to control the controllable power supply and adjust the electrical power applied to the bridge, thereby changing the flow of electrical current through the heater element so as to effect a variation in source temperature and hence heater element resistance, such that the bridge is returned to a balanced condition;

an electrical resistance element connectable in parallel with a leg of the bridge circuit other than the leg having the heater element connected therein to unbalance the bridge circuit and effect through the power supply control means a variation in source temperature; and a control element coupled to the electrical resistance element for effecting connection and disconnection of the resistance element to the bridge circuit to effect an unbalancing of the bridge circuit that results in a reduction in temperature of the alkali source from a reduction in temperature of the alkali source from a first elevated temperature at which active analysis is performed to a second, lower temperature that is below the temperature at which reactive substances passing through the detector will react with the alkali source, but is above the temperature at which condensation of non-volatile materials on the source occurs, and to effect a subsequent unbalancing of the bridge circuit after passage of the reactive substance that restores the temperature of the alkali source to the elevated temperature.

* * * * *